(12) United States Patent
Govari et al.

(10) Patent No.: US 12,415,028 B2
(45) Date of Patent: Sep. 16, 2025

(54) AUTOMATIC CONTROL OF PHACOEMULSIFICATION NEEDLE TRAJECTORY

(71) Applicant: JOHNSON & JOHNSON SURGICAL VISION, INC., Irvine, CA (US)

(72) Inventors: Assaf Govari, Haifa (IL); Christopher Thomas Beeckler, Brea, CA (US); Vadim Gliner, Haifa (IL); Ilya Sitnitsky, Nahariya (IL); Amit Fuchs, Hogla (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 686 days.

(21) Appl. No.: 17/748,091

(22) Filed: May 19, 2022

(65) Prior Publication Data
US 2023/0043082 A1 Feb. 9, 2023

Related U.S. Application Data

(60) Provisional application No. 63/230,741, filed on Aug. 7, 2021.

(51) Int. Cl.
*A61M 3/02* (2006.01)
*B06B 1/02* (2006.01)
(Continued)

(52) U.S. Cl.
CPC ........ *A61M 3/0275* (2013.01); *A61M 3/0202* (2021.05); *B06B 1/0284* (2013.01);
(Continued)

(58) Field of Classification Search
CPC .............. A61M 3/0275; A61M 3/0202; A61M 2205/3306; A61M 2205/3393;
(Continued)

(56) References Cited

U.S. PATENT DOCUMENTS

| | | | |
|---|---|---|---|
| 4,954,960 | A | 9/1990 | Lo et al. |
| 5,157,603 | A | 10/1992 | Scheller et al. |

(Continued)

FOREIGN PATENT DOCUMENTS

| | | | |
|---|---|---|---|
| DE | 3234621 A1 | 3/1984 | |
| EP | 0741554 A1 | 11/1996 | |

(Continued)

OTHER PUBLICATIONS

U.S. Appl. No. 17/357,587, titled, "Accurate Irrigation Rate Measurment System and Method," filed Jun. 24, 2021.
(Continued)

*Primary Examiner* — Ankit D Tejani
*Assistant Examiner* — Joshua Brendon Solomon

(57) ABSTRACT

A system and method that includes inserting a needle of a phacoemulsification handpiece into an eye of a patient and vibrating the needle in a first trajectory. Matter from the eye is aspirated via an aspiration line while the needle is vibrated in the first trajectory. An indication is received, of a vacuum level in the aspiration line. Determined is, that the vacuum level has changed by at least a preset vacuum level change, and in response vibrating the needle is switched to a second trajectory, different from the first trajectory.

10 Claims, 2 Drawing Sheets

(51) Int. Cl.
*B06B 1/06* (2006.01)
*G01R 27/02* (2006.01)
*G06F 3/04847* (2022.01)
*A61B 17/00* (2006.01)
*A61F 9/007* (2006.01)

(52) U.S. Cl.
CPC ............ *B06B 1/0614* (2013.01); *G01R 27/02* (2013.01); *G06F 3/04847* (2013.01); *A61B 2017/00199* (2013.01); *A61B 2217/005* (2013.01); *A61F 9/00745* (2013.01); *A61M 2205/3306* (2013.01); *A61M 2205/3393* (2013.01); *A61M 2205/581* (2013.01); *A61M 2205/587* (2013.01); *B06B 2201/76* (2013.01)

(58) Field of Classification Search
CPC ...... A61M 2205/581; A61M 2205/587; B06B 1/0284; B06B 1/0614; B06B 2201/76; B06B 3/00; G01R 27/02; G06F 3/04847; A61B 2017/00199; A61B 2217/005; A61F 9/00745

See application file for complete search history.

(56) References Cited

U.S. PATENT DOCUMENTS

| | | | |
|---|---|---|---|
| 5,160,317 A | 11/1992 | Costin | |
| 5,279,547 A | 1/1994 | Costin | |
| 5,733,256 A | 3/1998 | Costin | |
| 5,836,990 A | 11/1998 | Li | |
| 6,690,280 B2 | 2/2004 | Citrenbaum et al. | |
| 7,727,193 B2 | 6/2010 | Boukhny et al. | |
| 7,842,005 B2 | 11/2010 | Kadziauskas et al. | |
| 8,048,020 B2 | 11/2011 | Boukhny et al. | |
| 8,246,580 B2 | 8/2012 | Hopkins et al. | |
| 8,414,605 B2 | 4/2013 | Gordon et al. | |
| 8,523,812 B2 | 9/2013 | Boukhny et al. | |
| 8,597,228 B2 | 12/2013 | Pyles et al. | |
| 9,144,517 B2 | 9/2015 | Kuebler et al. | |
| 9,282,989 B2 | 3/2016 | Boukhny et al. | |
| 9,545,335 B2 | 1/2017 | Boukhny et al. | |
| 9,707,127 B2 | 7/2017 | Kadziauskas | |
| 9,999,710 B2 | 6/2018 | Ross et al. | |
| 10,045,882 B2 | 8/2018 | Balicki et al. | |
| 10,070,988 B2 | 9/2018 | McDonell et al. | |
| 10,219,940 B2 | 3/2019 | Raney et al. | |
| 10,368,760 B2 | 8/2019 | Hauck | |
| 10,453,571 B2 | 10/2019 | Teodorescu | |
| 10,463,780 B2 | 11/2019 | Mallough et al. | |
| 10,596,033 B2 | 3/2020 | Urich et al. | |
| 10,940,039 B2 | 3/2021 | Banko | |
| 11,141,313 B2 | 10/2021 | Zhang et al. | |
| 11,317,937 B2 | 5/2022 | Nott et al. | |
| 11,399,858 B2 | 8/2022 | Sawhney et al. | |
| 11,464,559 B2 | 10/2022 | Nott et al. | |
| 11,589,888 B2 | 2/2023 | Shelton, IV et al. | |
| 11,612,408 B2 | 3/2023 | Yates et al. | |
| 2004/0092800 A1 | 5/2004 | MacKool | |
| 2004/0193182 A1 | 9/2004 | Yaguchi et al. | |
| 2005/0209560 A1 | 9/2005 | Boukhny et al. | |
| 2005/0261628 A1 | 11/2005 | Boukhny et al. | |
| 2006/0079788 A1 | 4/2006 | Anderson et al. | |
| 2006/0100570 A1 | 5/2006 | Urich et al. | |
| 2006/0129140 A1 | 6/2006 | Todd et al. | |
| 2007/0073309 A1 | 3/2007 | Kadziauskas et al. | |
| 2007/0161972 A1 | 7/2007 | Felberg et al. | |
| 2008/0064935 A1 | 3/2008 | Wong et al. | |
| 2009/0118663 A1 | 5/2009 | Rockley et al. | |
| 2009/0182266 A1 | 7/2009 | Gordon et al. | |
| 2010/0069825 A1 | 3/2010 | Raney | |
| 2010/0118266 A1 | 5/2010 | Nixon | |
| 2010/0287127 A1 | 11/2010 | Claus et al. | |
| 2011/0015563 A1 | 1/2011 | Boukhny | |
| 2011/0092896 A1 | 4/2011 | Kuebler et al. | |
| 2011/0144641 A1 | 6/2011 | Dimalanta, Jr. et al. | |
| 2011/0313280 A1 | 12/2011 | Govari et al. | |
| 2012/0197215 A1* | 8/2012 | Akahoshi | A61F 9/00745 604/272 |
| 2012/0232466 A1 | 9/2012 | Kuebler et al. | |
| 2013/0211435 A1 | 8/2013 | Boukhny et al. | |
| 2014/0018724 A1 | 1/2014 | Staggs | |
| 2014/0114296 A1 | 4/2014 | Woodley et al. | |
| 2014/0257172 A1 | 9/2014 | Yalamanchili | |
| 2014/0316254 A1 | 10/2014 | Eversull et al. | |
| 2014/0323953 A1 | 10/2014 | Sorensen et al. | |
| 2015/0045806 A1 | 2/2015 | Urich et al. | |
| 2015/0073816 A1 | 3/2015 | Ha et al. | |
| 2015/0148615 A1 | 5/2015 | Brennan et al. | |
| 2015/0216726 A1 | 8/2015 | Kadziauskas et al. | |
| 2016/0175543 A1 | 6/2016 | Frankhouser et al. | |
| 2018/0028359 A1 | 2/2018 | Gordon et al. | |
| 2018/0092555 A1 | 4/2018 | Script | |
| 2018/0207330 A1 | 7/2018 | Ovchinnikov et al. | |
| 2018/0318131 A1 | 11/2018 | Boukhny et al. | |
| 2019/0099526 A1 | 4/2019 | Hajishah et al. | |
| 2019/0133822 A1 | 5/2019 | Banko | |
| 2019/0274748 A1 | 9/2019 | Danziger et al. | |
| 2020/0107957 A1 | 4/2020 | Zhang | |
| 2020/0107958 A1 | 4/2020 | Wong et al. | |
| 2020/0309760 A1 | 10/2020 | Durant | |
| 2021/0045918 A1 | 2/2021 | Raney | |
| 2021/0196515 A1 | 7/2021 | Urich | |
| 2021/0330493 A1* | 10/2021 | Steen | A61F 9/00745 |
| 2021/0361481 A1 | 11/2021 | Gliner et al. | |
| 2021/0401623 A1 | 12/2021 | Zhang et al. | |
| 2022/0008251 A1 | 1/2022 | Govari et al. | |
| 2022/0192876 A1 | 6/2022 | Algawi et al. | |
| 2022/0192878 A1 | 6/2022 | Algawi et al. | |
| 2022/0313489 A1 | 10/2022 | Hajishah et al. | |
| 2022/0362452 A1 | 11/2022 | Algawi et al. | |
| 2023/0039808 A1 | 2/2023 | Govari et al. | |
| 2023/0285189 A1 | 9/2023 | Govari | |
| 2023/0320897 A1 | 10/2023 | Hajishah et al. | |
| 2024/0099884 A1 | 3/2024 | Govari et al. | |
| 2024/0130891 A1 | 4/2024 | Govari | |
| 2024/0398618 A1 | 12/2024 | Gliner et al. | |

FOREIGN PATENT DOCUMENTS

| | | |
|---|---|---|
| EP | 0956840 A2 | 11/1999 |
| EP | 1935383 A1 | 6/2008 |
| EP | 1765190 B1 | 7/2008 |
| EP | 1743309 B1 | 10/2011 |
| EP | 3448235 A2 | 3/2019 |
| JP | 4126304 B2 | 7/2008 |
| WO | 9211814 A1 | 7/1992 |
| WO | 2008016870 A2 | 2/2008 |
| WO | 2010014937 A1 | 2/2010 |
| WO | 2016122790 A1 | 8/2016 |
| WO | 2019069201 A1 | 4/2019 |
| WO | 2021119616 A1 | 6/2021 |
| WO | 2023170486 A1 | 9/2023 |

OTHER PUBLICATIONS

U.S. Appl. No. 16/727,100, titled "Phacoemulsification Apparatus," filed Dec. 26, 2019.

* cited by examiner

AUTOMATIC CONTROL OF PHACOEMULSIFICATION NEEDLE TRAJECTORY

CROSS-REFERENCE TO RELATED APPLICATION

This application claims the benefit of U.S. Provisional Patent Application 63/230,741, filed Aug. 7, 2021, whose disclosure is incorporated herein by reference.

FIELD OF THE DISCLOSURE

The present disclosure relates generally to phacoemulsification systems, and particularly to control of a phacoemulsification probe tip trajectory.

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

The present disclosure will be more fully understood from the following detailed description of the examples thereof, taken together with the drawings in which:

DETAILED DESCRIPTION OF EXAMPLES

Overview

A phacoemulsification system is used to remove a natural eye lens with a cataract by breaking it into smaller pieces and emulsifying the pieces using a handpiece comprising a hollow needle. The eye lens fragments are then aspirated from the eye through the needle.

During aspiration some emulsified particles may stick to the external wall of the phacoemulsification needle, creating what is termed a "lollipop" effect. Removal of the needle from the eye while particles are stuck to the needle wall may cause trauma to the eye.

Examples of the present disclosure that are described herein provide a method for correcting the possible presence of stuck particles. When the needle first contacts the eye lens, the vacuum level in the line rises (i.e., the pressure decreases). The vacuum level remains high as the needle penetrates into the lens and divides the lens into sections. The vacuum level drops when emulsified material from the sections begins to be aspirated into the aspiration line, and this is a time when emulsified particles may stick to the needle wall.

In one example, a processor looks for the drop in vacuum level described above, and if the drop is detected, the processor toggles the ultrasonic vibration trajectory of the needle within the eye to a different trajectory for a preset period of time, after which the trajectory is switched back to its initial trajectory. The initial trajectory may be longitudinal (with respect to the longitudinal axis of the needle), and the latter trajectory may be elliptical (e.g., a combination of longitudinal and transverse (or side to side) movement with respect to the longitudinal axis of the needle). Toggling in this manner may remove particles stuck to the needle.

More generally, the processor may toggle between a number of different trajectories of vibrating the phacoemulsification needle, e.g., longitudinal, planar (e.g., transverse), torsional, elliptical, as well as in combinations and subcombinations of such trajectories.

System Description

Figure 1:
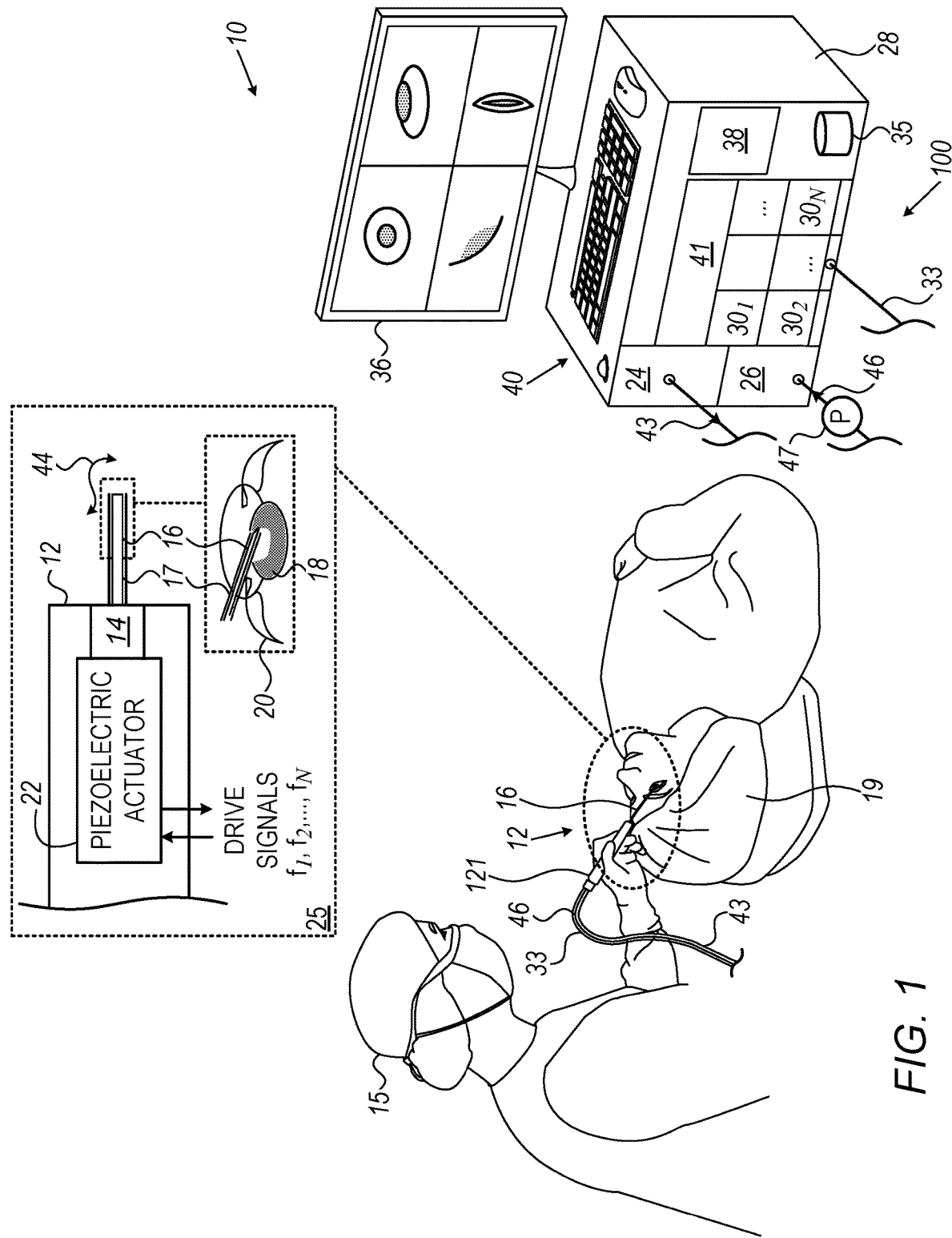
FIG. 1 is a pictorial view of a phacoemulsification system constructed to operate in accordance with an example of the present disclosure.

FIG. 1 is a pictorial view of a phacoemulsification system 10 constructed to operate in accordance with an example of the present disclosure. FIG. 1 includes an inset 25, and, as shown in the figure and the inset system 10, includes a phacoemulsification probe/handpiece 12 comprising a needle 16. Needle 16 is configured to be inserted into a lens capsule 18 of an eye 20 of a patient 19. Needle 16 is mounted on a horn 14 of probe 12, and is shown in inset 25 as a straight needle. However, any suitable needle may be used with phacoemulsification probe 12, for example, a curved or bent tip needle commercially available from Johnson & Johnson Surgical Vision, Irvine, CA, USA. A physician 15 holds handpiece 12 by a handle 121 so as to perform a phacoemulsification procedure on the eye 20 of patient 19. The physician may activate the handpiece using a foot pedal (not illustrated in FIG. 1).

Handpiece 12 comprises a piezoelectric actuator 22, which is configured to vibrate horn 14 and needle 16 in one or more resonant vibration modes of the combined horn and needle element. During the phacoemulsification procedure, the vibration of needle 16 is used to break a cataract into small pieces.

During the phacoemulsification procedure, an irrigation sub-system 24, which may be located in a console 28, pumps irrigation fluid from an irrigation reservoir to an irrigation sleeve 17 surrounding at least a portion of needle 16, so as to irrigate the eye 20. The combined structure of needle 16 and irrigation sleeve 17 is called hereinafter a "phacoemulsification tip." The fluid is pumped via a tubing line (irrigation line) 43 running from the console 28 to the probe 12. Irrigation sub-system 24 is described in more detail below.

An aspiration sub-system 26, also typically located in console 28, aspirates eye fluid and waste matter (e.g., emulsified parts of the cataract) from the patient's eye 20 via needle 16 to a collection receptacle (not shown). Aspiration sub-system 26 comprises a pump which produces a vacuum that is connected from the sub-system to probe 12 by an aspiration tubing line 46. A gauge or sensor 47 in line 46 measures the aspiration vacuum and/or pressure. Gauge 47 may be in any convenient location in line 46, including, but not limited to, a location in or in proximity to handpiece 12 or a location in or in proximity to the console 28.

Irrigation sub-system 24 and aspiration sub-system 26 are both controlled by a processor 38. The processor controls the flow volume rate at which the irrigation sub-system pumps fluid. The processor also controls the vacuum, pressure, and/or aspiration rate of the aspiration sub-system, using a pressure reading from gauge 47.

Some or all of the functions of processor 38 may be combined in a single physical component or, alternatively, implemented using multiple physical components. The physical components may comprise hard-wired or programmable devices, or a combination of the two. In some examples, at least some of the functions of processor 38 may be carried out by suitable software stored in a memory 41. The software may be downloaded to a device in electronic form, over a network, for example. Alternatively, or additionally, the software may be stored in tangible, non-transitory computer-readable storage media, such as optical, magnetic, or electronic memory.

Processor 38 may receive user-based commands via a user interface 40, which may include setting and/or adjusting a vibration mode, power level, duty cycle, and/or a frequency of piezoelectric actuator 22, setting and/or adjusting a stroke amplitude of needle 16, and setting and/or adjusting an irrigation rate, an aspiration rate, and/or an aspiration vacuum of irrigation sub-system 24 and aspiration sub-system 26. Additionally, or alternatively, processor 38 may receive user-based commands from controls located in handpiece 12, to, for example, select a trajectory 44, or another trajectory, for needle 16. The implementation of a trajectory such as trajectory 44 is further described below.

Processor 38 may present results of the phacoemulsification procedure on a display 36. In an example, user interface 40 and display 36 may be one and the same, such as a touch screen graphical user interface.

The system illustrated in FIG. 1 may include further elements, which are omitted for clarity of presentation. For example, physician 15 typically performs the procedure using a stereo-microscope or magnifying glasses, neither of which are shown. Physician 15 may use other surgical tools, in addition to probe 12, which are also not shown to maintain clarity and simplicity.

Console 28 further comprises a multi-channel piezoelectric drive system 100 comprising drive modules 30₁, 30₂, . . . 30$_N$, each coupled, using wiring in a cable 33, to a stack of piezoelectric crystals of piezoelectric actuator 22. Drive modules 30₁, 30₂, . . . 30$_N$, generically termed drive modules 30, are controlled by processor 38 and convey phase-controlled driving signals via cable 33 to piezoelectric actuator 22. In response, piezoelectric actuator 22 vibrates needle 16, which performs a vibrational/ultrasound trajectory 44, the trajectory typically comprising one, or a combination, of longitudinal, transverse, and/or torsional ultrasonic vibrations synchronized one with the other.

Method of Automatic Control of Phacoemulsification Needle Trajectory

As noted above, during the phacoemulsification procedure performed by physician 15, emulsified matter from the eye 20 of patient 19 is aspirated by aspiration sub-system 26. However, there are some instances during the procedure when the emulsified matter may stick to the external wall of the needle, causing what is termed a "lollipop" effect. It may be difficult or even impossible for the physician to know that material is stuck to the needle, so that attempts to remove the needle from the eye with the stuck material may cause trauma. Even if the physician is aware of material being stuck to the needle, the only way to remove the material may be to insert another tool, e.g., a chopper or vacuum probe, to collect the material.

Figure 2:
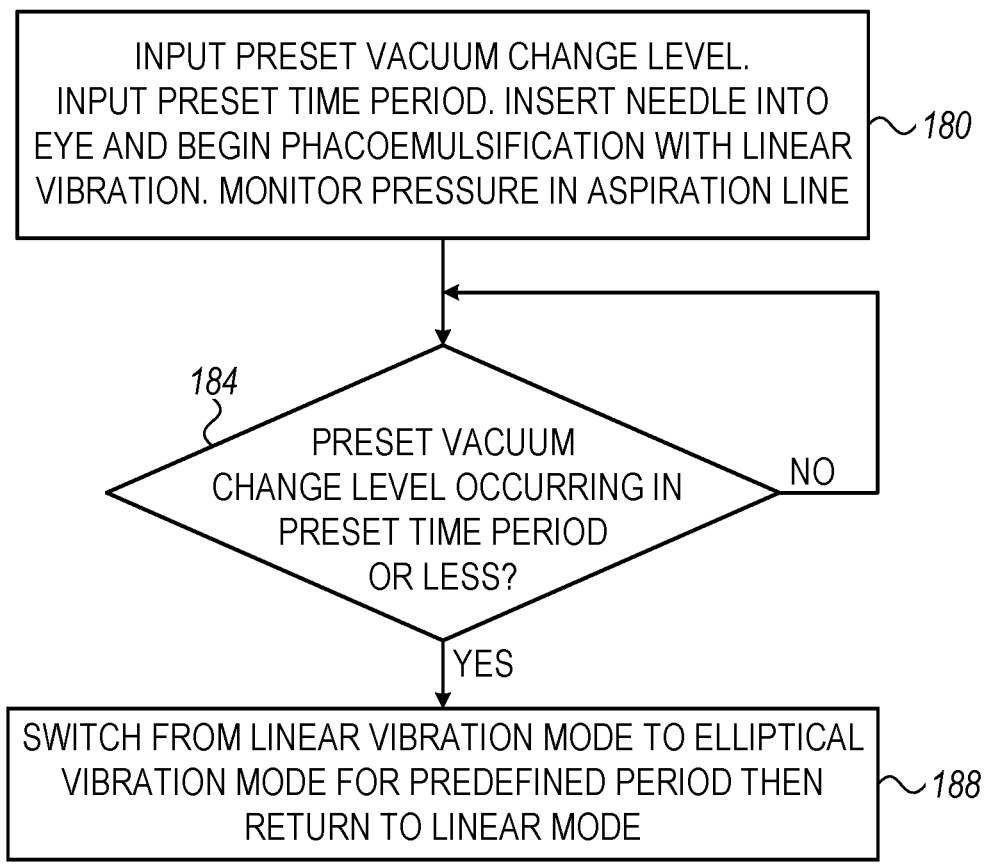
FIG. 2 is a flow chart that schematically illustrates a method for controlling a phacoemulsification needle, to prevent emulsified particles from sticking, in accordance with an example of the present disclosure.

FIG. 2 is a flow chart that schematically illustrates a method for controlling a phacoemulsification needle (such as needle 16), to prevent emulsified particles from sticking, in accordance with an example of the present disclosure. Implementing the steps of the flow chart prevents the lollipop effect from occurring.

During a phacoemulsification procedure, once needle 16 begins to engage with the eye lens, the vacuum level in the aspiration line typically increases due to partial or complete occlusion of the distal end of the needle. During an occlusion the vacuum level may increase to a relatively high level, i.e., the pressure falls to a relatively low level. Typical pressure values for this stage range from approximately −300 mmHg to approximately −650 mmHg. The levels stay generally constant until the needle begins to break the lens into sections.

As the needle breaks up the sections it begins to form emulsified particles, which are aspirated into aspiration line 46. The aspiration of the emulsified particles at this time reduces the vacuum level in the line, for example, by at least 50 mmHg (i.e., the pressure increases by at least 50 mmHg). This is the time period when some of the particles may stick to the wall of the needle. As is described below, steps of the flow chart check for this reduction in vacuum level, which typically occurs over a relatively short period of time of approximately 3 msec. If this kind of reduction is observed, the flow chart describes actions which may reduce the likelihood of emulsified particles from sticking to the wall of the needle.

In an initial step 180 of the flow chart, physician 15 inserts needle 16 in the lens capsule 18 of patient 19 and provides instructions to processor 38 so that the processor configures drive modules 30 to generate trajectory 44 as a first trajectory, herein assumed to comprise a substantially longitudinal trajectory. Such a longitudinal trajectory may be efficient for initially breaking up the eye lens into small sections.

Processor 38 is also provided with a preset vacuum change level, e.g., 50 mmHg, corresponding to the reduction in vacuum level described above, as well as with a preset period of time, e.g., 3 msec, corresponding to the short time period referred to above. During initial step 180, processor 38 monitors the pressure in aspiration line 46 using pressure gauge 47.

In a decision step 184, while monitoring the pressure in the aspiration line, the processor checks if a vacuum reduction, corresponding to the preset vacuum change level of step 180, has occurred within the preset time period. If decision step 184 returns negative ("No"), i.e., no vacuum reduction is detected within the preset time period, control returns to step 184, so that the processor continues to monitor the aspiration line pressure iteratively.

If decision step 184 returns positive ("Yes"), i.e., the processor detects that a vacuum reduction is occurring, control transfers to a switching step 188.

In switching step 188 of the flow chart, the processor reconfigures drive modules 30 to generate trajectory 44 as a second trajectory, different from the first trajectory, e.g., a substantially elliptical trajectory (combination of longitudinal and transverse). The elliptical trajectory may shake off material stuck to needle 16. Processor 38 maintains the switch to the second trajectory for a predefined period of time, herein assumed to be a period between approximately 10 μs and approximately 10 msec.

The example flow chart shown in FIG. 2 is chosen purely for the sake of conceptual clarity. For example, additional steps, such as audiovisual alert may be included.

EXAMPLES

Example 1

A method comprises inserting a needle (16) of a phacoemulsification handpiece (12) into an eye (20) of a patient (19), and vibrating the needle in a first trajectory. Matter from the eye (20) is aspirated via an aspiration line (46) while the needle is vibrated in the first trajectory. An indication is received, of a vacuum level in the aspiration line (46). Determined is, that the vacuum level has changed by at least a preset vacuum level change, and in response vibrating the needle is switched to a second trajectory, different from the first trajectory.

Example 2

The method according to example 1, wherein the first trajectory comprises a longitudinal vibration, and the second trajectory comprises an elliptical vibration.

Example 3

The method according to any of examples 1 and 2, wherein switching to vibrate the needle (16) in the second trajectory comprises vibrating the needle in the second trajectory for a predefined period of time.

Example 4

The method according to any of examples 1 through 3, further comprising returning to vibrating the needle (16) in the first trajectory upon completion of the predefined period of time.

Example 5

The method according to any of examples 1 through 4, wherein determining that the vacuum level has changed comprises determining that the vacuum level has changed by at least the preset vacuum level change during a time period less than or equal to a preset time period.

Example 6

A system (10) includes a needle (16) of a phacoemulsification handpiece (12), an aspiration line (46), and a processor (38). The needle is configured for insertion into an eye (20) of a patient (19), and being vibrated in a first trajectory. The aspiration line is configured for aspiration of matter from the eye via the needle while the needle is vibrated in the first trajectory. The processor (38) is configured to (i) receive an indication of a vacuum level in the aspiration line, and (ii) determine that the vacuum level has changed by at least a preset vacuum level change, and in response switching to vibrate the needle in a second trajectory, different from the first trajectory.

Although the examples described herein mainly address phacoemulsification, the methods and systems described herein can also be used in other surgical applications that may require a multi-channel piezoelectric resonant system to drive a moving member, such as ultrasonic blades, and other types of actuators.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
 inserting a needle of a phacoemulsification handpiece into an eye of a patient, and vibrating the needle in a first trajectory;
 aspirating matter from the eye via an aspiration line while the needle is vibrated in the first trajectory;
 receiving an indication of a vacuum level in the aspiration line; and
 determining that the vacuum level has changed by at least a preset vacuum level change, and in response switching to vibrate the needle in a second trajectory, different from the first trajectory;
 wherein determining that the vacuum level has changed by at least a preset vacuum level change comprises determining that the vacuum level has changed by at least the preset vacuum level change during a time period less than or equal to a preset time period.

2. The method according to claim 1, wherein the first trajectory comprises a longitudinal vibration, and the second trajectory comprises an elliptical vibration.

3. The method according to claim 1, wherein switching to vibrate the needle in the second trajectory comprises vibrating the needle in the second trajectory for a predefined period of time.

4. The method according to claim 3, further comprising returning to vibrating the needle in the first trajectory upon completion of the predefined period of time.

5. A system, comprising:
 a needle of a phacoemulsification handpiece configured for insertion into an eye of a patient, and being vibrated in a first trajectory;
 an aspiration line coupled with the needle and configured for aspiration of matter from the eye via the needle while the needle is vibrated in the first trajectory; and
 a processor, which is configured to:
  receive an indication of a vacuum level in the aspiration line; and
  determine that the vacuum level has changed by at least a preset vacuum level change, and in response switching to vibrate the needle in a second trajectory, different from the first trajectory;
  wherein the processor is configured to determine that the vacuum level has changed by determining that the vacuum level has changed by at least the preset vacuum level change during a time period less than or equal to a preset time period.

6. The system according to claim 5, wherein the first trajectory comprises a longitudinal vibration, and the second trajectory comprises an elliptical vibration.

7. The system according to claim 5, wherein the processor is configured to switch to vibrate the needle in the second trajectory by vibrating the needle in the second trajectory for a predefined period of time.

8. The system according to claim 7, wherein the processor is further configured to return to vibrating the needle in the first trajectory upon completion of the predefined period of time.

9. The method according to claim 1, wherein the first trajectory is a longitudinal trajectory and the second trajectory is an elliptical trajectory.

10. The system according to claim 5, wherein the first trajectory is a longitudinal trajectory and the second trajectory is an elliptical trajectory.

* * * * *